(12) United States Patent
Wang et al.

(10) Patent No.: US 7,488,419 B1
(45) Date of Patent: Feb. 10, 2009

(54) WATER FAUCET CONTAINING WATER MIXED WITH OZONE

(76) Inventors: Hsiang-Shih Wang, 110, Hsiao-Yang Rd., Changhua City, Changhua County (TW); Shih-Chang Chen, 8F-1, No. 110, Sec. 2, Hankou Rd., Hefu Li, Situn District, Taichung City (TW)

(*) Notice: Subject to any disclaimer, the term of this patent is extended or adjusted under 35 U.S.C. 154(b) by 83 days.

(21) Appl. No.: 11/749,439

(22) Filed: May 16, 2007

(51) Int. Cl.
*C02F 1/78* (2006.01)
(52) U.S. Cl. ............... 210/198.1; 261/76; 261/DIG. 42; 261/DIG. 75
(58) Field of Classification Search .......... 210/449, 210/198.1; 239/407, 418, 423, 425, 428.5; 261/DIG. 42, DIG. 75
See application file for complete search history.

(56) References Cited

U.S. PATENT DOCUMENTS

| | | | | |
|---|---|---|---|---|
| 2,778,800 A | * | 1/1957 | Sheahan | 261/49 |
| 6,030,586 A | * | 2/2000 | Kuan | 422/186.07 |
| 6,135,146 A | * | 10/2000 | Koganezawa et al. | 137/554 |
| 6,521,194 B2 | * | 2/2003 | Yeh | 422/186.12 |
| 2006/0266683 A1 | * | 11/2006 | Sung | 210/198.1 |

* cited by examiner

*Primary Examiner*—Tony G Soohoo
*Assistant Examiner*—Paul J Durand
(74) *Attorney, Agent, or Firm*—Alan Kamrath; Kamrath & Associates PA

(57) ABSTRACT

A water faucet includes a faucet body, an ozone generator, a control ring, a nozzle head, an aerator, a mounting seat and a control valve. Thus, the water flowing outwardly from the nozzle head of the water faucet is mixed with ozone supplied by ozone generator to provide sterilizing, disinfecting, bleaching and odorizing functions by provision of the ozone.

20 Claims, 6 Drawing Sheets

WATER FAUCET CONTAINING WATER MIXED WITH OZONE

BACKGROUND OF THE INVENTION

1. Field of the Invention

The present invention relates to a water faucet and, more particularly, to a water faucet for supplying water for use with a user.

2. Description of the Related Art

A conventional water faucet comprises a faucet body provided with a water outlet pipe, a nozzle head mounted on the water outlet pipe of the faucet body to inject the water of the water outlet pipe of the faucet body outwardly, and a control handle mounted on the water outlet pipe of the faucet body to open or close the water flow from the nozzle head. However, the water in the water faucet may contain impurities or harmful materials, thereby causing danger to the user who drinks the water.

BRIEF SUMMARY OF THE INVENTION

In accordance with the present invention, there is provided a water faucet, comprising a faucet body provided with a water outlet pipe, an ozone generator provided with an air guide hose extended into a hollow inside of the water outlet pipe of the faucet body, a control ring mounted in the water outlet pipe of the faucet body and having an air inlet hole connected to the air guide hose of the ozone generator, an air outlet hole connected to the air inlet hole and a plurality of water channels connected to the hollow inside of the water outlet pipe of the faucet body, a nozzle head mounted on the water outlet pipe of the faucet body to retain the control ring in the water outlet pipe of the faucet body and having a water inlet port connected to the water channels of the control ring, a water outlet port connected to the water inlet port, an aerating space connected between the water inlet port and the water outlet port and an air conducting hole connected between the air outlet hole of the control ring and the aerating space, and an aerator mounted in the aerating space of the nozzle head and connected between the water inlet port, the water outlet port and the air conducting hole of the nozzle head.

The primary objective of the present invention is to provide a water faucet containing water mixed with ozone.

Another objective of the present invention is to provide a water faucet, wherein the water flowing outwardly from the nozzle head of the water faucet is mixed with ozone to provide sterilizing, disinfecting, bleaching and odorizing functions by provision of the ozone.

A further objective of the present invention is to provide a water faucet, wherein the control valve of the water faucet prevents the water in the nozzle head from flowing back into the air guide hose of the ozone generator.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

DETAILED DESCRIPTION OF THE INVENTION

Figure 1:
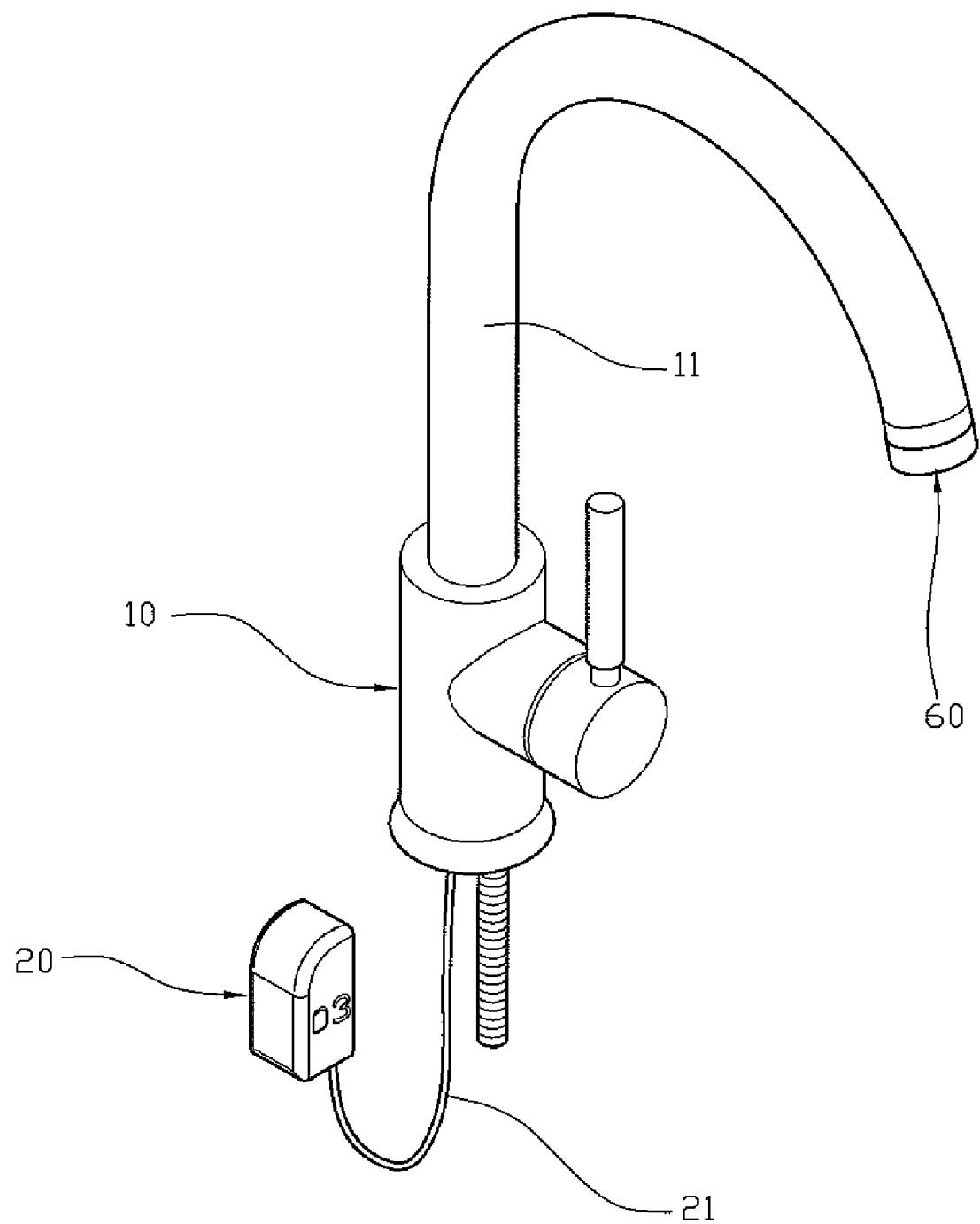
FIG. 1 is a perspective view of a water faucet in accordance with the preferred embodiment of the present invention.
Figure 2:
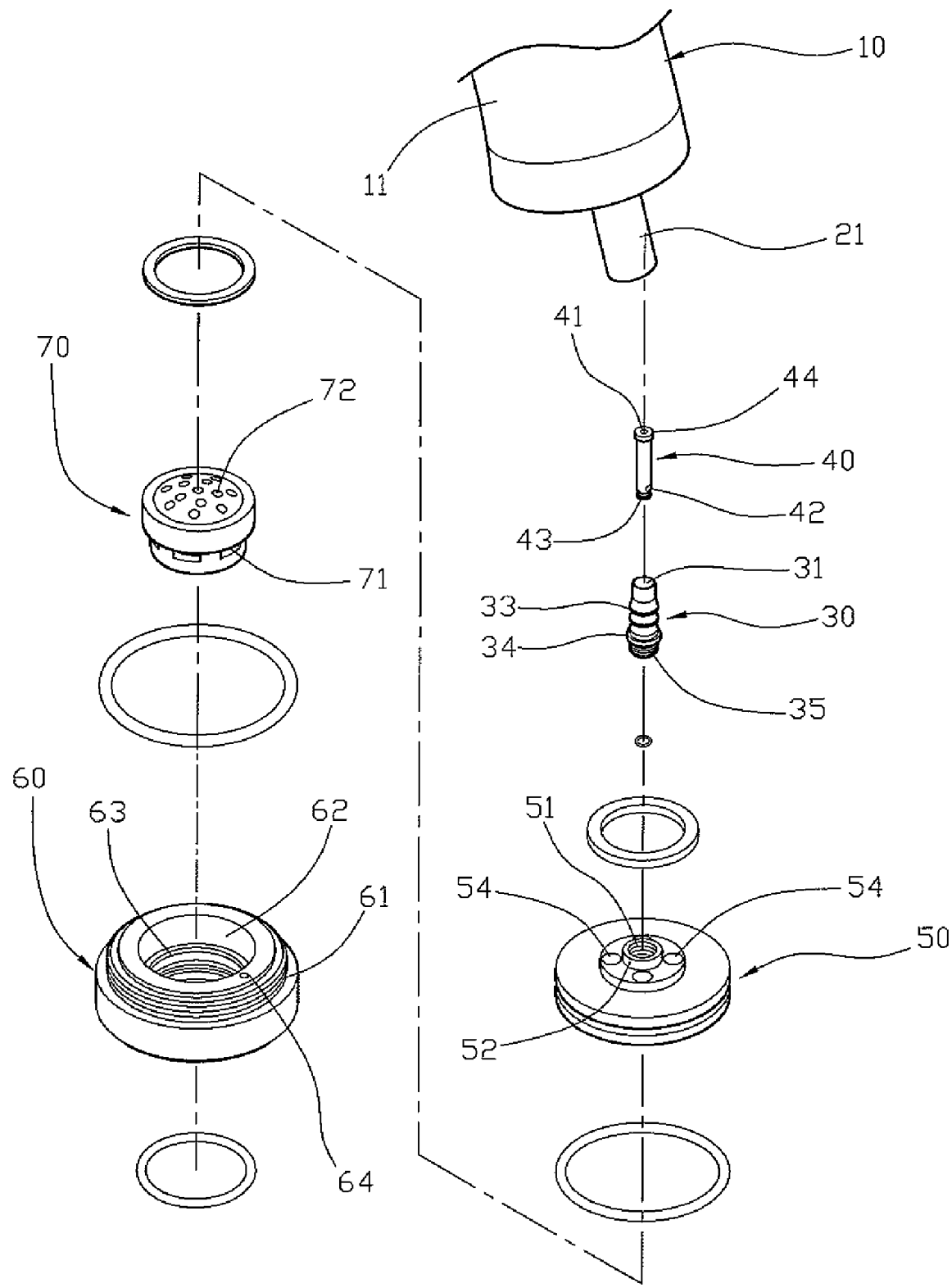
FIG. 2 is an exploded perspective view of the water faucet as shown in FIG. 1.
Figure 3:
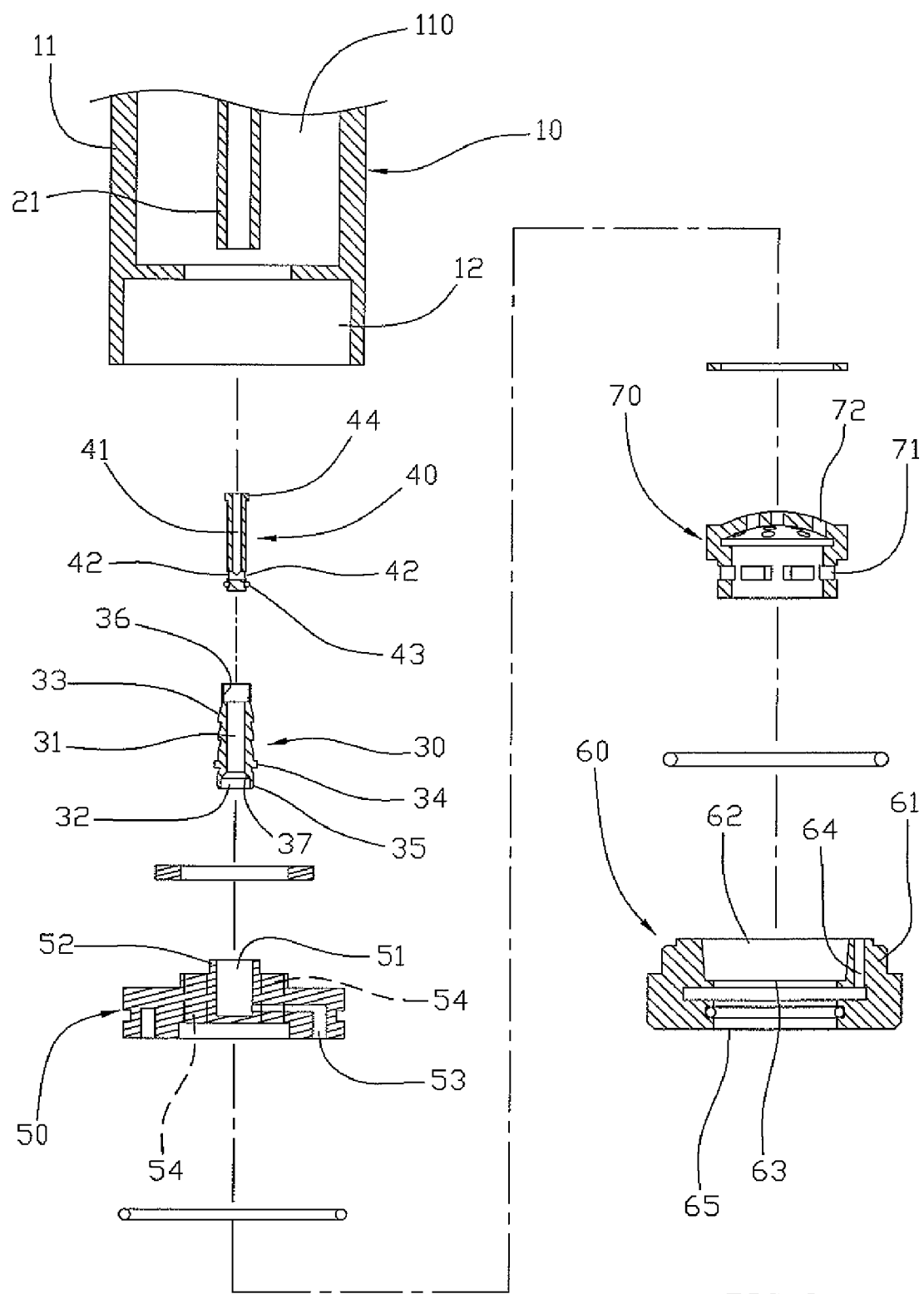
FIG. 3 is a front cross-sectional view of the water faucet as shown in FIG. 2.
Figure 4:
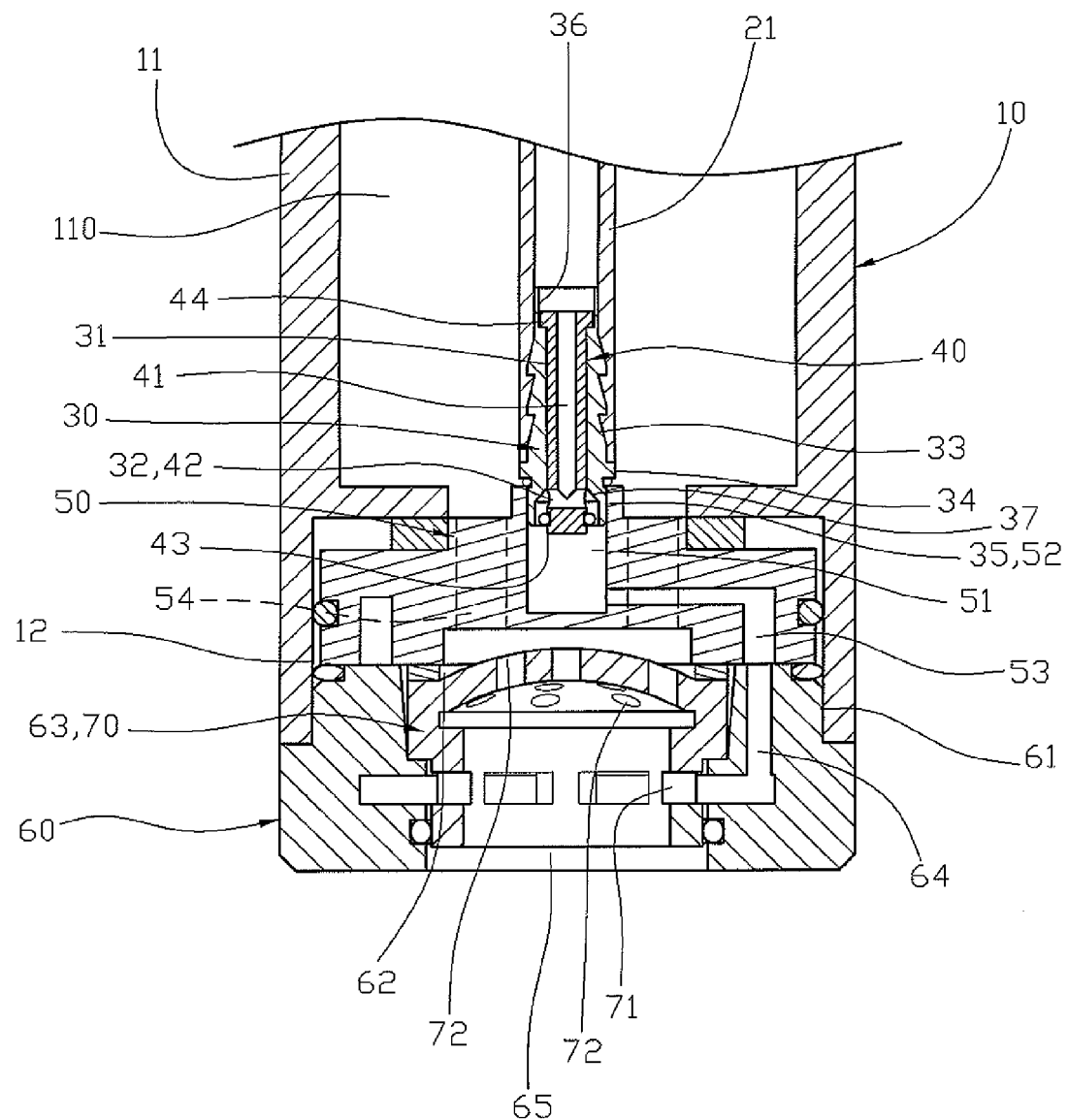
FIG. 4 is a front cross-sectional view of the water faucet as shown in FIG. 1.

Referring to the drawings and initially to FIGS. 1-4, a water faucet in accordance with the preferred embodiment of the present invention comprises a faucet body 10 provided with a water outlet pipe 11, an ozone generator 20 provided with an air guide hose 21 extended into a hollow inside 110 of the water outlet pipe 11 of the faucet body 10, a control ring 50 mounted in the water outlet pipe 11 of the faucet body 10 and having an air inlet hole 51 connected to the air guide hose 21 of the ozone generator 20, an air outlet hole 53 connected to the air inlet hole 51 and a plurality of water channels 54 connected to the hollow inside 110 of the water outlet pipe 11 of the faucet body 10, a nozzle head 60 mounted on the water outlet pipe 11 of the faucet body 10 to retain the control ring 50 in the water outlet pipe 11 of the faucet body 10 and having a water inlet port 62 connected to the water channels 54 of the control ring 50, a water outlet port 65 connected to the water inlet port 62, an aerating space 63 connected between the water inlet port 62 and the water outlet port 65 and an air conducting hole 64 connected between the air outlet hole 53 of the control ring 50 and the aerating space 63, and an aerator 70 mounted in the aerating space 63 of the nozzle head 60 and connected between the water inlet port 62, the water outlet port 65 and the air conducting hole 64 of the nozzle head 60.

The water outlet pipe 11 of the faucet body 10 has a distal end having an inner wall provided with a locking portion 12 located adjacent to the air guide hose 21 of the ozone generator 20.

The control ring 50 has a first side having a central portion formed with the air inlet hole 51 and a second side having a periphery formed with the air outlet hole 53. The air inlet hole 51 of the control ring 50 has an end face formed with an outwardly extended threaded mounting stud 52. The water channels 54 of the control ring 50 are separated from the air inlet hole 51 and the air outlet hole 53.

The nozzle head 60 has a first side formed with the water inlet port 62 and a second side having a periphery formed with the water outlet port 65. The first side of the nozzle head 60 has a periphery formed with the air conducting hole 64 which is separated from the water inlet port 62 and the water outlet port 65. The first side of the nozzle head 60 has an outer wall provided with a locking section 61 locked in the locking portion 12 of the water outlet pipe 11 of the faucet body 10 and rested on the second side of the control ring 50.

The aerator 70 has an inside formed with a plurality of water conducting holes 72 connected between the water inlet port 62 and the water outlet port 65 of the nozzle head 60 and has a periphery formed with a plurality of air inlet ports 71 connected between the air conducting hole 64 of the nozzle head 60 and the water conducting holes 72.

The water faucet further comprises a mounting seat 30 mounted between the air guide hose 21 of the ozone generator 20 and the control ring 50 and having an inside formed with a guide hole 31 having a first end connected to the air guide hose 21 of the ozone generator 20 and a second end formed with an enlarged control space 32 connected to the air inlet hole 51 of the control ring 50, and a control valve 40 movably mounted in the guide hole 31 of the mounting seat 30 and having an inside formed with an air channel 41 connected to the air guide hose 21 of the ozone generator 20 and a periphery formed with an air connecting hole 42 that is connected between the air channel 41 and the control space 32 of the mounting seat 30 and a protruding seal ring 43 that is movable to seal the control space 32 of the mounting seat 30 to interrupt a connection between the air connecting hole 42 and the control space 32 of the mounting seat 30.

The mounting seat 30 has a first end provided with a serrated insert 33 inserted into a distal end of the air guide hose 21 of the ozone generator 20 and a second end provided with a threaded plug 35 screwed into the mounting stud 52 of the control ring 50. The insert 33 of the mounting seat 30 has a distal end formed with an outwardly extending stop flange 34 rested on the distal end of the air guide hose 21 of the ozone generator 20. The first end of the guide hole 31 of the mounting seat 30 is formed with a stepped limit hole 36. The mounting seat 30 has a tapered sealing face 37 located between the guide hole 31 and the control space 32 to limit the seal ring 43 of the control valve 40.

The control valve 40 is made of a flexible material. The control valve 40 has a first end provided with the air connecting hole 42 and the seal ring 43 and a second end provided with an enlarged limit flange 44 movable and limited in the limit hole 36 of the mounting seat 30. The air connecting hole 42 of the control valve 40 is located between the air channel 41 and the seal ring 43. The seal ring 43 of the control valve 40 is movable in the control space 32 of the mounting seat 30. Thus, the control valve 40 is movable in the guide hole 31 of the mounting seat 30 between a first position where the seal ring 43 of the control valve 40 is detachable from the sealing face 37 of the mounting seat 30 to connect the air connecting hole 42 to the control space 32 of the mounting seat 30 and a second position where the seal ring 43 of the control valve 40 presses the sealing face 37 of the mounting seat 30 to interrupt the connection between the air connecting hole 42 and the control space 32 of the mounting seat 30.

Figure 5:
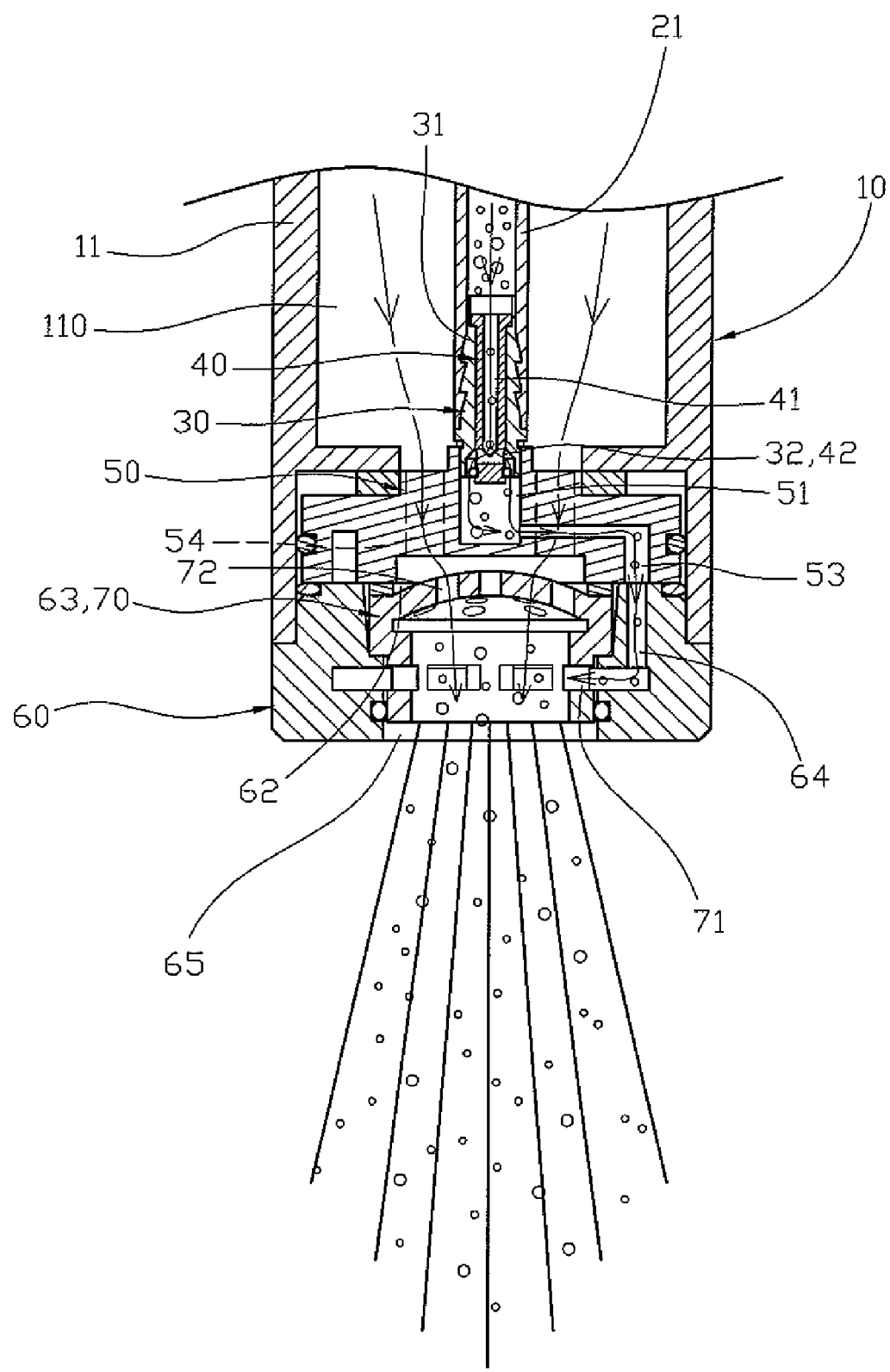
FIG. 5 is a schematic operational view of the water faucet as shown in FIG. 1 in use.

In operation, referring to FIG. 5 with reference to FIGS. 1-4, the water in the hollow inside 110 of the water outlet pipe 11 of the faucet body 10 in turn flows through the water channels 54 of the control ring 50, the water inlet port 62 of the nozzle head 60, the water conducting holes 72 of the aerator 70 and the water outlet port 65 of the nozzle head 60 and is injected outwardly from the water outlet port 65 of the nozzle head 60 for use with a user.

At this time, the ozone from the air guide hose 21 of the ozone generator 20 in turn flows through the air channel 41 of the control valve 40, the air connecting hole 42 of the control valve 40, the guide hole 31 of the mounting seat 30, the control space 32 of the mounting seat 30, the air inlet hole 51 of the control ring 50, the air outlet hole 53 of the control ring 50, the air conducting hole 64 of the nozzle head 60 and the air inlet ports 71 of the aerator 70 into the aerator 70 to mix with the water contained in the aerator 70 so that the water contains multiple ozone bubbles. After the faucet body 10 stops operating, the ozone generator 20 also stops operating to stop supply of the ozone.

Figure 6:
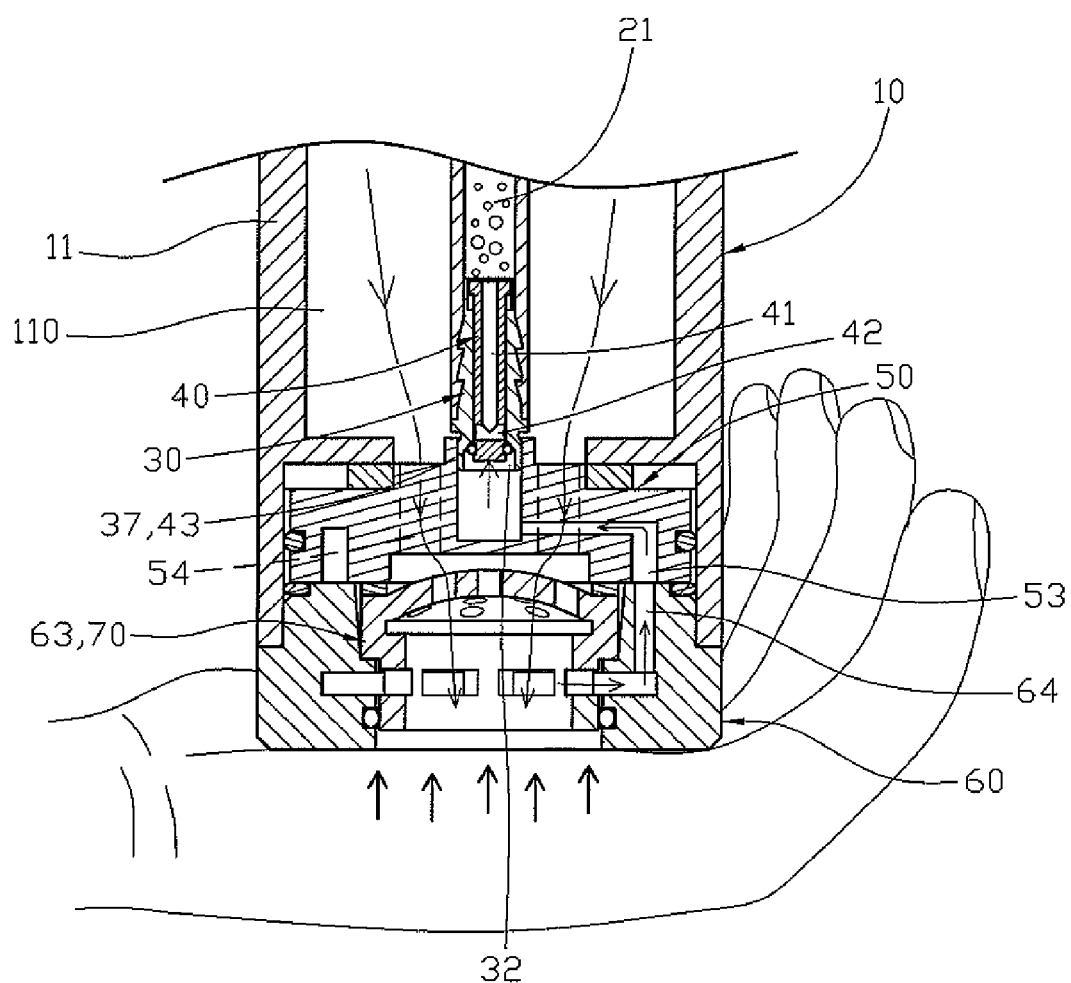
FIG. 6 is another schematic operational view of the water faucet as shown in FIG. 1.

As shown in FIG. 6, when the nozzle head 60 is sealed by a naughty child, the water in the nozzle head 60 flows back to push the control valve 40 upward so that the seal ring 43 of the control valve 40 is movable upward to press the sealing face 37 of the mounting seat 30 to interrupt the connection between the air connecting hole 42 and the control space 32 of the mounting seat 30 and to seal the mounting seat 30, the control valve 40 and the air guide hose 21 of the ozone generator 20 to prevent the water in the nozzle head 60 from flowing back into the air guide hose 21 of the ozone generator 20.

Accordingly, the water flowing outwardly from the nozzle head 60 of the water faucet is mixed with ozone to provide sterilizing, disinfecting, bleaching and odorizing functions by provision of the ozone. In addition, the control valve 40 of the water faucet prevents the water in the nozzle head 60 from flowing back into the air guide hose 21 of the ozone generator 20.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

The invention claimed is:

1. A water faucet, comprising:
   a faucet body provided with a water outlet pipe;
   an ozone generator provided with an air guide hose extended into a hollow inside of the water outlet pipe of the faucet body;
   a control ring mounted in the water outlet pipe of the faucet body and having an air inlet hole connected to the air guide hose of the ozone generator, an air outlet hole connected to the air inlet hole and a plurality of water channels connected to the hollow inside of the water outlet pipe of the faucet body;
   a nozzle head mounted on the water outlet pipe of the faucet body to retain the control ring in the water outlet pipe of the faucet body and having a water inlet port connected to the water channels of the control ring, a water outlet port connected to the water inlet port, an aerating space connected between the water inlet port and the water outlet port and an air conducting hole connected between the air outlet hole of the control ring and the aerating space;
   an aerator mounted in the aerating space of the nozzle head and connected between the water inlet port, the water outlet port and the air conducting hole of the nozzle head.

2. The water faucet in accordance with claim 1, wherein the control ring has a first side having a central portion formed with the air inlet hole and a second side having a periphery formed with the air outlet hole.

3. The water faucet in accordance with claim 2, wherein:
   the water outlet pipe of the faucet body has a distal end having an inner wall provided with a locking portion;
   the first side of the nozzle head has an outer wall provided with a locking section locked in the locking portion of the water outlet pipe of the faucet body and rested on the second side of the control ring.

4. The water faucet in accordance with claim 3, wherein the locking portion of the water outlet pipe of the faucet body is located adjacent to the air guide hose of the ozone generator.

5. The water faucet in accordance with claim 1, wherein the water channels of the control ring are separated from the air inlet hole and the air outlet hole.

6. The water faucet in accordance with claim 1, wherein the nozzle head has a first side formed with the water inlet port and a second side having a periphery formed with the water outlet port.

7. The water faucet in accordance with claim 6, wherein the first side of the nozzle head has a periphery formed with the air conducting hole.

8. The water faucet in accordance with claim 1, wherein the air conducting hole of the nozzle head is separated from the water inlet port and the water outlet port.

9. The water faucet in accordance with claim 1, wherein the aerator has an inside formed with a plurality of water conducting holes connected between the water inlet port and the water outlet port of the nozzle head and has a periphery formed with a plurality of air inlet ports connected between the air conducting hole of the nozzle head and the water conducting holes.

10. The water faucet in accordance with claim 9, further comprising:
- a mounting seat mounted between the air guide hose of the ozone generator and the control ring and having an inside formed with a guide hole having a first end connected to the air guide hose of the ozone generator and a second end formed with an enlarged control space connected to the air inlet hole of the control ring;
- a control valve movably mounted in the guide hole of the mounting seat and having an inside formed with an air channel connected to the air guide hose of the ozone generator and a periphery formed with an air connecting hole that is connected between the air channel and the control space of the mounting seat and a protruding seal ring that is movable to seal the control space of the mounting seat to interrupt a connection between the air connecting hole and the control space of the mounting seat.

11. The water faucet in accordance with claim 10, wherein the mounting seat has a first end provided with a serrated insert inserted into a distal end of the air guide hose of the ozone generator.

12. The water faucet in accordance with claim 11, wherein:
- the air inlet hole of the control ring has an end face formed with an outwardly extended threaded mounting stud;
- the mounting seat has a second end provided with a threaded plug screwed into the mounting stud of the control ring.

13. The water faucet in accordance with claim 11, wherein the insert of the mounting seat has a distal end formed with an outwardly extending stop flange rested on the distal end of the air guide hose of the ozone generator.

14. The water faucet in accordance with claim 10, wherein the control valve has a first end provided with the air connecting hole and the seal ring.

15. The water faucet in accordance with claim 14, wherein:
- the first end of the guide hole of the mounting seat is formed with a stepped limit hole;
- the control valve has a second end provided with an enlarged limit flange movable and limited in the limit hole of the mounting seat.

16. The water faucet in accordance with claim 10, wherein the mounting seat has a tapered sealing face located between the guide hole and the control space to limit the seal ring of the control valve.

17. The water faucet in accordance with claim 16, wherein the control valve is movable in the guide hole of the mounting seat between a first position where the seal ring of the control valve is detachable from the sealing face of the mounting seat to connect the air connecting hole to the control space of the mounting seat and a second position where the seal ring of the control valve presses the sealing face of the mounting seat to interrupt the connection between the air connecting hole and the control space of the mounting seat.

18. The water faucet in accordance with claim 10, wherein the air connecting hole of the control valve is located between the air channel and the seal ring.

19. The water faucet in accordance with claim 10, wherein the seal ring of the control valve is movable in the control space of the mounting seat.

20. The water faucet in accordance with claim 10, wherein ozone from the air guide hose of the ozone generator in turn flows through the air channel of the control valve, the air connecting hole of the control valve, the guide hole of the mounting seat, the control space of the mounting seat, the air inlet hole of the control ring, the air outlet hole of the control ring, the air conducting hole of the nozzle head and the air inlet ports of the aerator.

* * * * *